US010552950B2

(12) United States Patent
Balagurusamy et al.

(10) Patent No.: US 10,552,950 B2
(45) Date of Patent: Feb. 4, 2020

(54) MAPPING AND ENCODING GEMOLOGICAL FEATURES

(71) Applicant: INTERNATIONAL BUSINESS MACHINES CORPORATION, Armonk, NY (US)

(72) Inventors: Venkat K. Balagurusamy, Suffern, NY (US); Donna N. Eng Dillenberger, Yorktown Heights, NY (US); Joseph W. Ligman, Wilton, CT (US)

(73) Assignee: International Business Machines Corporation, Armonk, NY (US)

( * ) Notice: Subject to any disclaimer, the term of this patent is extended or adjusted under 35 U.S.C. 154(b) by 151 days.

(21) Appl. No.: 15/814,706

(22) Filed: Nov. 16, 2017

(65) Prior Publication Data

US 2018/0342053 A1  Nov. 29, 2018

Related U.S. Application Data

(60) Provisional application No. 62/511,256, filed on May 25, 2017.

(51) Int. Cl.
*G06T 7/00* (2017.01)
*G06T 7/11* (2017.01)
(Continued)

(52) U.S. Cl.
CPC ............... *G06T 7/0002* (2013.01); *G06T 7/11* (2017.01); *G06T 7/13* (2017.01); *G06T 7/60* (2013.01);
(Continued)

(58) Field of Classification Search
CPC ....... G06T 3/60; G06T 7/0002; G06T 7/0004; G06T 7/11; G06T 7/13; G06T 7/55;
(Continued)

(56) References Cited

U.S. PATENT DOCUMENTS 4,900,147 A  2/1990 Bowley et al.
6,813,007 B2  11/2004 Lapa et al.
(Continued)

FOREIGN PATENT DOCUMENTS

CN  106662566 A  5/2017
JP  2011122934 A  6/2011
(Continued)

OTHER PUBLICATIONS

International Search Report and Written Opinion for International Application No. PCT/IB2017/057723, Applicant's or agent's file reference P201700877, dated Jan. 31, 2018, International filing date Dec. 7, 2017, 10 pages.

(Continued)

*Primary Examiner* — Katrina R Fujita
(74) *Attorney, Agent, or Firm* — John Noh

(57) ABSTRACT

Embodiments of the present invention disclose a method, computer program product, and system for mapping one or more inclusions in a mineral crystal. A set of image data associated with the mineral crystal is receiving. The received set of image data is analyzed. One or more inclusions associated with the mineral crystal is identified based on the analyzed image data. The identified one or more inclusions of the mineral crystal are mapped to a tree structure representing the surface of the mineral crystal. The mapped one or more inclusions are encoded as a chain-code associated with the mineral crystal. A radial distance between a center of mass value of the mineral crystal and a center of mass value of the identified one or more inclusions is calculated and a mineral crystal fingerprint is generated.

20 Claims, 6 Drawing Sheets

(51) Int. Cl.
*G06T 7/13* (2017.01)
*G06T 15/20* (2011.01)
*G06T 7/60* (2017.01)
*G06T 3/60* (2006.01)

(52) U.S. Cl.
CPC .............. *G06T 15/205* (2013.01); *G06T 3/60* (2013.01); *G06T 2200/08* (2013.01); *G06T 2207/20081* (2013.01)

(58) Field of Classification Search
CPC ..... G06T 7/60; G06T 15/205; G06T 2200/08; G06T 2207/20081; G06T 2207/30108
See application file for complete search history.

(56) References Cited

U.S. PATENT DOCUMENTS

| | | | | |
|---|---|---|---|---|
| 7,239,739 | B2* | 7/2007 | Lapa | G01N 21/87 |
| | | | | 382/141 |
| 7,307,714 | B2 | 12/2007 | Cyr et al. | |
| 7,755,072 | B2 | 7/2010 | Porat | |
| 8,098,368 | B2 | 1/2012 | Shlezinger et al. | |
| 8,270,719 | B2* | 9/2012 | Ellawand | G01N 21/41 |
| | | | | 356/30 |
| 9,151,717 | B2* | 10/2015 | Schnitzer | G01N 21/87 |
| 9,292,966 | B2 | 3/2016 | Sivovolenko | |
| 9,494,533 | B2 | 11/2016 | Orlov et al. | |
| 10,318,515 | B2* | 6/2019 | Verboven | G06F 16/2282 |
| 2003/0223054 | A1 | 12/2003 | Warwick | |
| 2005/0117145 | A1 | 6/2005 | Altman et al. | |
| 2016/0004926 | A1* | 1/2016 | Kerner | G01B 11/24 |
| | | | | 348/46 |
| 2016/0070723 | A1* | 3/2016 | Horiuchi | G01N 21/87 |
| | | | | 235/375 |
| 2016/0167164 | A9 | 6/2016 | Rosario et al. | |
| 2016/0203495 | A1* | 7/2016 | Koh | G06Q 10/06 |
| | | | | 705/317 |
| 2017/0241913 | A1* | 8/2017 | Gu | G01N 21/87 |
| 2017/0276612 | A1* | 9/2017 | Gaywala | G01N 33/381 |
| 2018/0372647 | A1* | 12/2018 | Brenner | G01N 21/87 |

FOREIGN PATENT DOCUMENTS

| | | |
|---|---|---|
| WO | 9961890 A1 | 12/1999 |
| WO | 2007023444 A3 | 3/2007 |
| WO | 2016092300 A1 | 6/2016 |

OTHER PUBLICATIONS

Moshe, "An Image Processing Approach to Diamond Inspection and Evaluation", MS32 3D crystal imaging, 24th European Crystallographic Meeting, ECM24, Marrakech, 2007, Acta Cryst. (2007). A63, p. s79.

Diehl et al., "X-Ray Fingerprinting Routine for Cut Diamonds", Gems & Gemology, vol. 40, No. 1, pp. 40-57, © 2004 Gemological Institute of America, Spring 2004.

* cited by examiner

MAPPING AND ENCODING GEMOLOGICAL FEATURES

BACKGROUND

The present invention relates generally to the field of gemological analysis, and more particularly to mapping gemological features.

Many natural or manmade stones or mineral formations are usable as gems. Some examples include diamonds, emeralds, or rubies. A typical feature of a precious stone includes inclusions of other materials, for example, impurities, defects, or imperfections, in the precious stone. For example, diamonds may contain black carbon specs, emeralds may contain strands or specs of differently colored minerals, and other such impurities may comprise an inclusion. Cracks, chipped edges or corners, thickness or thinness of a cut or facet, and variations in refractive index are also examples of imperfections, or inclusions.

SUMMARY

Embodiments of the present invention disclose a method, computer program product, and system for mapping one or more inclusions in a mineral crystal. A set of image data associated with the mineral crystal is receiving. The received set of image data is analyzed, wherein analyzing the received set of image data further comprises segmenting the image data via machine learned parameters. One or more inclusions associated with the mineral crystal is identified based on the analyzed image data, wherein inclusions are non-linear isolated regions on a surface of the mineral crystal. The identified one or more inclusions of the mineral crystal are mapped to a tree structure representing the surface of the mineral crystal. The mapped one or more inclusions are encoded as a chain-code associated with the mineral crystal. A radial distance between a center of mass value of the mineral crystal and a center of mass value of the identified one or more inclusions is calculated and a mineral crystal fingerprint is generated, wherein the mineral crystal fingerprint is based on at least the encoded one or more inclusions and the calculated radial distance.

DETAILED DESCRIPTION

Figure 1:
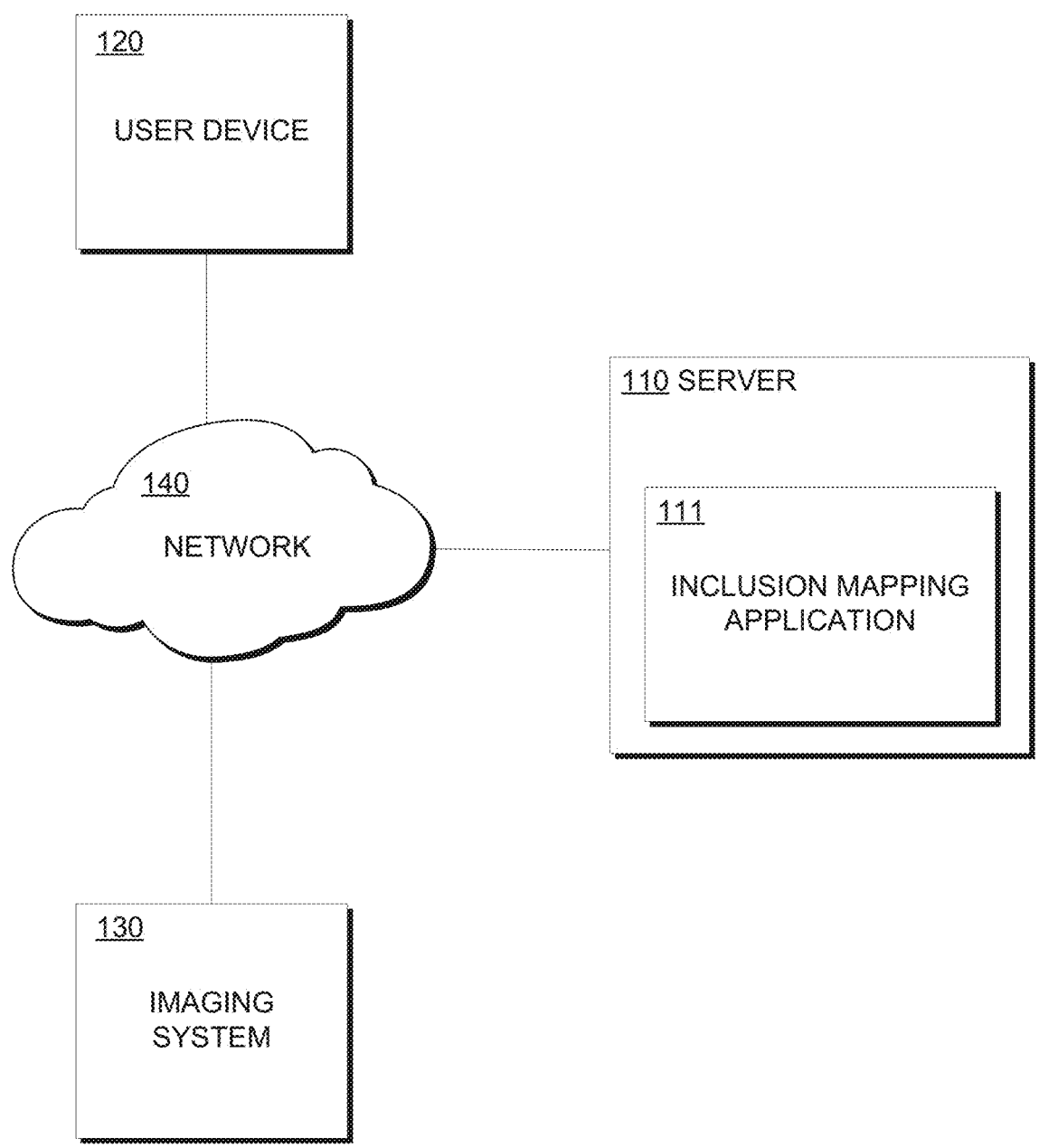
FIG. 1 is a functional block diagram illustrating a distributed data processing environment, in accordance with an embodiment of the present invention.

Embodiments of the present invention relate to the field of computing, and more particularly to mapping and encoding gemological features. The following described exemplary embodiments provide a system, method, and program product to, among other things, mapping one or more inclusions in a mineral crystal or diamond. Therefore, the present embodiment has the capacity to improve the technical field of diamond mapping and encoding by automatically generating diamond digital fingerprints in order to, for example, make an appraisal for, or the tracking of, diamonds. To aid in appraisals and tracking of diamonds, it may be advantageous to be able to identify inclusions and generate a digital map of the inclusions from various visual sources.

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. Rather, these exemplary embodiments are provided so that this disclosure will be thorough and complete and will fully convey the scope of this invention to those skilled in the art. In the description, details of well-known features and techniques may be omitted to avoid unnecessarily obscuring the presented embodiments.

References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Almost all diamonds have small imperfections visible on the surface. These imperfections are caused naturally as a diamond is formed under extreme pressure and heat. The size and amount of imperfections visible on the surface of the diamond often determine the overall grade and monetary value of the stone. This grading procedure is typically a manual process where a human grader inspects and maps out the imperfections of the diamond with the help of microscopes, and other tools, and contributes this to an overall quality grade. The clarity grade of a particular gemstone, such as a diamond, is predominantly determined by the size and quality of inclusions. Most typically, gemstones are assigned a grade based on a clarity scale: Flawless (FL), Internally Flawless (IF), Very Very Slightly Included (VVS1 VVS2), Very Slightly Included (VS1 VS2), Slightly Included (SI1 SI2), Included (I1 I2 I3). As part of the grading process, the inclusions are typically mapped to a Diamond Plot, which is a graphical representation of the diamond's surface used for recording the type and position of each flaw or inclusion. Today, inspecting, plotting and mapping the diamond flaws is a manual process requiring a human expert gemologist.

Inclusions may appear as bright or dark spots on an image of the diamond when viewed under a microscope. Typically, a micro-lens setup can be used to capture high resolution digital images of the diamonds including any bright spots or dark spots. It is noted that the typical inspection and grading is carried out with a microscope having a predetermined standard magnification, such as, for example, 10×. Furthermore, any one diamond may have inclusions or imperfections that may not be visible during the standard inspection and grading process. Thus the inspection and grading process is limited to those imperfections or inclusions which are visible or recognizable under the standard inspection process.

It may be advantageous to have a system capable of creating a three-dimensional computer generated model of a gemstone, such as a diamond, from one or more of the following inputs: a set of two-dimensional images, metrics including crown angle, pavilion angle, table size, cutlet size, star length, lower-girdle length, girdle thickness, girdle facets, camera metrics, lighting metrics and other to be determined information needed to generate the model. The computer generated three-dimensional model may emulate realistic lighting conditions. Machine learning analysis of the image data may be used to generate the computer rendered model and inclusion locations may be determined from analyzing the image data inputs. In various embodiments of the present invention, a manual inclusion map may be generated during a machine learning training period. The inclusions may be mapped on the generated model and displayed to a user.

The present invention relates generally to the field of gemological analysis, and more particularly to mapping gemological features. One way to map gemological features may include image data analysis in order to determine the location of inclusions in the gemstone. Embodiments by which to analyze image data in order to determine the location of inclusions in the gemstone are described in detail below by referring to the accompanying drawings FIGS. 1-4. Although embodiments of the present invention are directed at mapping gemological features of gemstones generally, for exemplary purposes only, the following description is directed at mapping and encoding gemological features of diamonds specifically. FIG. 1 depicts a functional block diagram illustrating a distributed data processing environment, generally designated 100, in accordance with one embodiment of the present invention. The distributed data processing environment 100 may include server 110, user device 120, imaging system 130 all connected via network 140.

Server 110 and user device 120 may be a laptop computer, tablet computer, netbook computer, personal computer (PC), a desktop computer, a smart phone, or any programmable electronic device capable of communicating with various components and devices distributed data processing environment 100, for example, server 110, user device 120, and imaging system 130, via network 140. In various embodiments, server 110 may be a separate server or series of servers, a database, or other data storage, internal or external to user device 120 and imaging system 130.

In various embodiments, user device 120 may act generally to host an application capable of display, in a graphical user interface, or communicate over a network, for example network 140, via a web browser. In various embodiments of the invention, user device 120 may communicate with other computing devices within distributed data processing environment 100. User device 120 may communicate requests over network 140 for, for example, a request for a digital fingerprint or identification of a mineral crystal, or diamond, fingerprint generated by server 110 based on image data received by server 110 from imaging system 130.

Imaging system 130 can be lens-based system, video system, or any system capable of generating image data and communicating the generated image data to other devices, for example, server 110 and user device 120 over network 140.

In various embodiments, server 110 includes inclusion mapping application 111, as described in more detail below with reference to FIG. 2. Inclusion mapping application 111 may act generally to receive a set of image data, for example, from imaging system 130 via server 110. Inclusion mapping application 111 may analyze the received image data of diamonds and utilize computer vision algorithms and machine learning parameters to derive the locations of inclusions or defects based on the received image data. Inclusion mapping application 111 may map the surface of the diamond and generate a 3D model of the diamond based on the image data that includes the identified inclusions.

In an alternate embodiment of the present invention, imaging system 130 may include mapping application 111 in a data storage device and the invention presented below may be conducted within imaging system 130.

Additionally, in an alternate embodiment of the present invention, user device 120 may include a lensing system for capturing image data and a data store that includes inclusion mapping application 111, in order to perform the functions of server 110 and imaging system 130.

Figure 2:
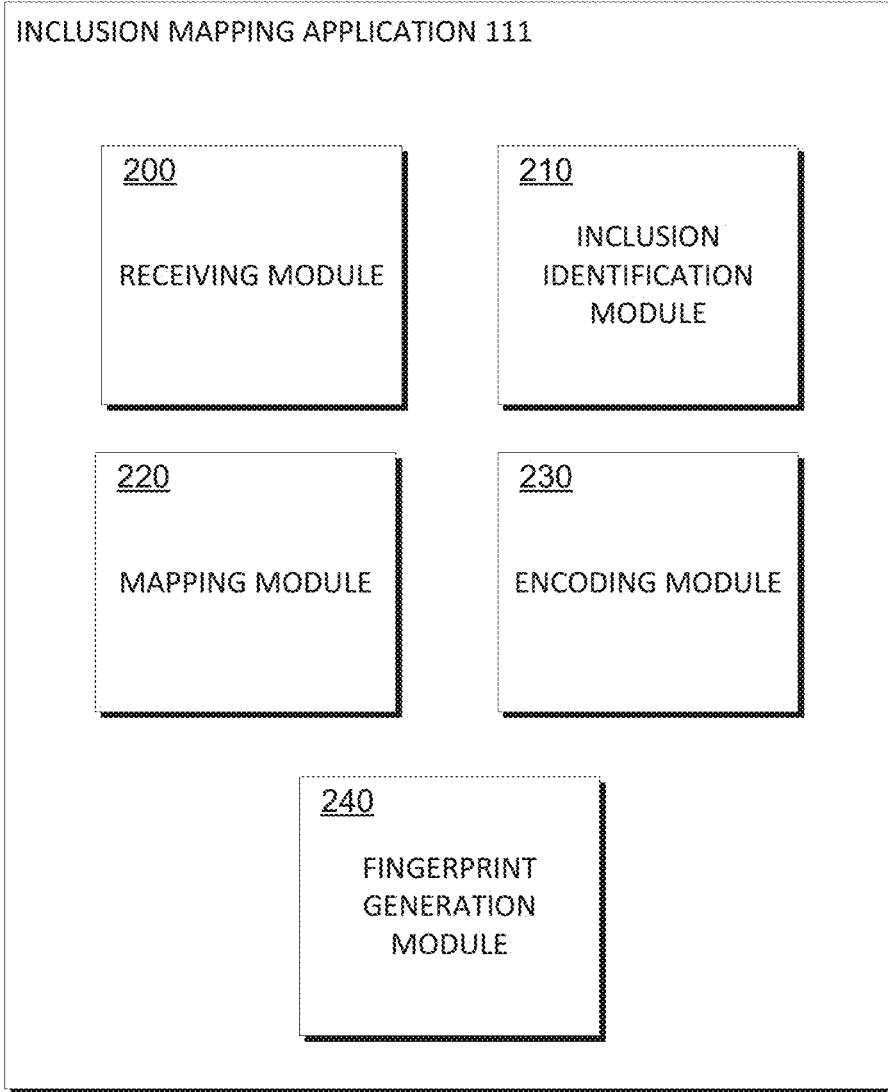
FIG. 2 depicts a functional block diagram illustrating the components of an application within the distributed data processing environment, in accordance with an embodiment of the present invention.

FIG. 2 depicts a functional block diagram illustrating the components of inclusion mapping application 111 on server 110, within the distributed data processing environment 100, in accordance with an embodiment of the present invention. Inclusion mapping application 111 includes receiving module 200, inclusion identification module 210, mapping module 220, encoding module 230, and fingerprint generation module 240.

In reference to FIGS. 1 and 2, receiving module 200 may receive requests for diamond digital fingerprints and sets of image data, for example, from user device 120 and imaging system 130 respectively. Receiving module 200 may identify any metadata associated with the receive image data in order to determine the resolution and magnification factor of the image data. In various embodiments, the resolution and magnification values captured by imaging system 130 may be predetermined, for example, image data captured by imaging system 130 may have a resolution of 1920×1080 pixels and a magnification factor of 10×. Receiving module 200 may communicate the received image data and associated metadata to inclusion identification module 210. The image data may represent a measurement of visible light reflected from the surface of the associated mineral crystal or diamond. It should be appreciated that the reflected visible light is meant to be electromagnetic radiation at a wavelength of 400 nm to 700 nm.

Inclusion identification module 210 may receive image data from receiving module 200. Inclusion identification module 210 may analyze the received image data in order to identify inclusions or defects in the diamond based on the image data. Inclusion identification module 210 may use machine learning or computer vision segmentation in order to partition the received image data into multiple segments. In various embodiments, segmentation uses a grid layer on the received image and which allows for the identification of objects with boundaries within an image. Inclusion identification module 210 may determine that the identified objects or boundaries represent inclusions within the diamond.

In various embodiments, inclusion identification module 210 may generate a three-dimensional model based on the received image data using rasterization. Rasterization is the description of an image in a vector graphics format and converting it into a raster image for output on a video display or printer, for example, a display on user device 120. In various embodiments, the raster image may be produced in real-time as three-dimensional renderings of received image data. Ray tracing may be used for the received still image data rendering. Ray tracing is a rendering technique for generating an image by tracing the path of light as pixels in an image plane and simulating the effects of its encounters with virtual objects. It may be advantageous to use ray tracing with diamond images as ray tracing is capable of simulating reflection and refraction, scattering, and dispersion phenomena, for example, chromatic aberrations.

The model may include lighting conditions by applying rasterization or ray tracing to the model based on the received image data. The surface of the diamond and internal inclusions may be included in the model using the segmentation analysis and identifying inclusion as non-linear isolated areas on the diamond surface. In various embodiments, inclusion identification module 210 may communicate the model data to mapping module 220.

Mapping module 220 may receive diamond model data from inclusion identification module 210 that includes surface data and inclusion data. Mapping module 220 may map the inclusions identified by inclusion identification module 210 on to a tree structure representing the two-dimensional surface of the diamond at a configurable magnification.

Encoding module 230 may receive mapped inclusions from mapping module 220 and encode the inclusions using Freeman's chain-code algorithm. The algorithm may calculate the radial distance associated with the mapped inclusions by calculating a contour of an inclusion by tracing in a direction, or direction vector, e.g., counterclockwise, beginning with a selected starting point, or reference vector, and each contour step is computed and stored. Particularly, starting from the reference vector, the distance between the center of mass and the contour is measured in defined angular steps and plotted as a function of the polar angle. The three-dimensional precise encoding of the three-dimensional defect, generated in this manner from an embodiment may provide increased efficiency in defining inclusions in the diamonds as compared to presently available approximate sketches of a two-dimensional outline of an inclusion based on human observation of the gem under a microscope.

Figure 6:
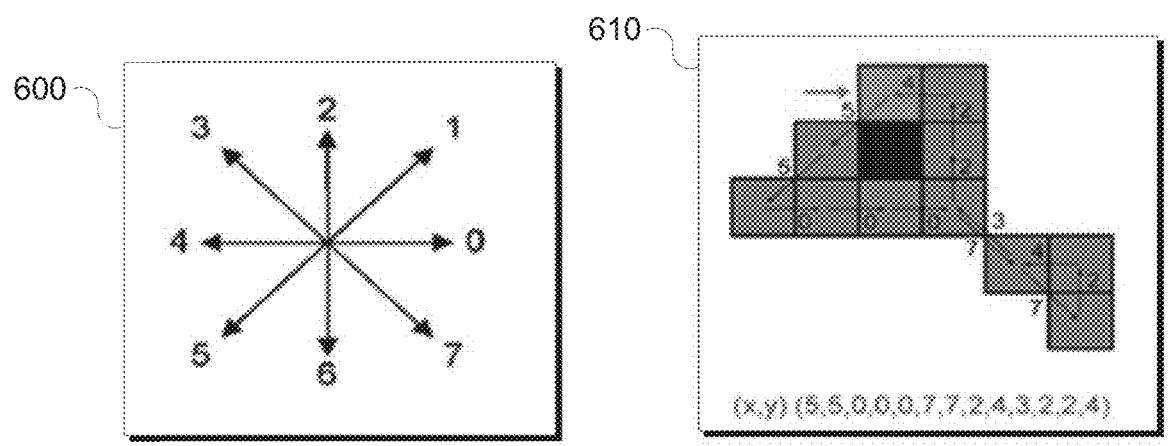
FIG. 6 depicts an exemplary diagram of a Freeman's chain-code and an exemplary diagram of chain-coding.

FIG. 6 depicts an exemplary diagram of a Freeman's chain-code, generally designated 600 and an exemplary diagram of chain-coding, designated chain-code 610. Freeman's chain-code 600 represents the value associated with the direction of movement in chain-code 610. In various embodiments, chain-code 610 starts in the shaded block above the black block and the value of the direction of each of the subsequent contour steps may be stored.

Chain code and radial distance algorithms. A chain code is a lossless compression algorithm for monochrome images. The basic principle of chain codes is to separately encode each connected component, or identified inclusion, in the image. For each such region, a point on the boundary is selected and its coordinates are transmitted. Encoding module 230 may move along the boundary of the region and, at each step, transmits direction of this movement. The three-dimensional precise encoding of the three-dimensional defect, generated in this manner from an embodiment may improve the defining of the defect in the diamond as compared to presently available approximate sketches of a two-dimensional outlines of defects based on human observation of the gem under a microscope.

Fingerprint generation module 240 may generate a digital fingerprint based received image data, the mapped inclusions, and encoded inclusions. The generated fingerprint may include metadata tags that associate the fingerprint with the mineral crystal, or diamond, that was captured in the image data.

Figure 3:
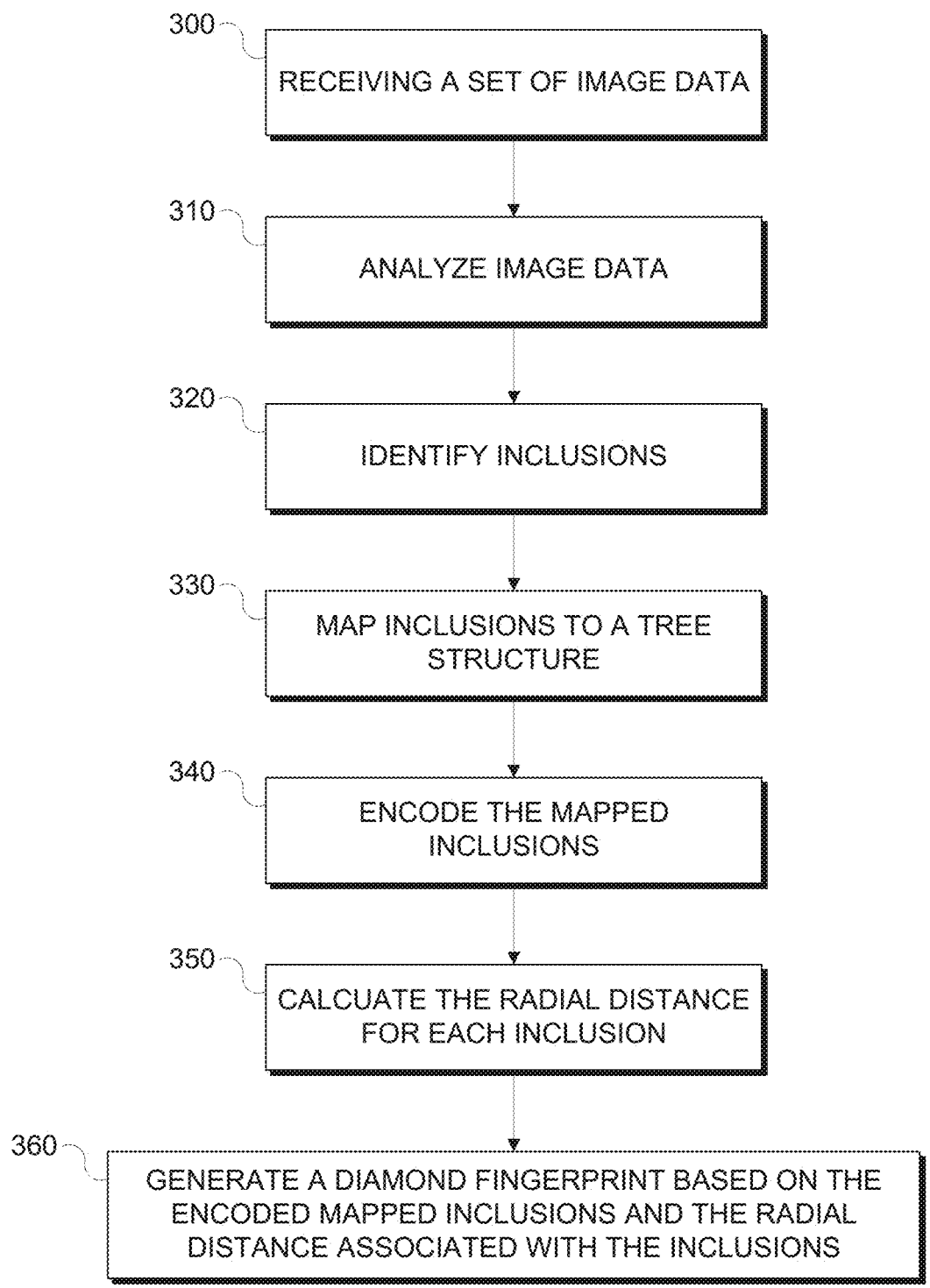
FIG. 3 is a flowchart depicting operational steps of a mapping application, on a server computer within the data processing environment of FIG. 1, in accordance with an embodiment of the present invention.

FIG. 3 depicts a flowchart depicting operational steps of inclusion mapping application 111, on server 110 within the data processing environment 100 of FIG. 1, in accordance with an embodiment of the present invention.

Receiving module 200 receives a set of image data (block 300), for example, from imaging system 130, via server 110. In various embodiments, receiving module 200 receives image data from user device 120 with an associated request for a mineral crystal fingerprint. Receiving module 200 communicates the received image data to inclusion identification module 210.

Inclusion identification module 210 analyzes the received image data (block 310). Inclusion identification module 210 analyzes the image data by segmentation of the received image data. In various embodiments, inclusion identification module 210 generates a three-dimensional model of the diamond associated with the image based on received two-dimensional image data. Inclusion identification module 210 rotates each image of the set of image data such that the surface of each image is perpendicular to a viewing plane. Inclusion identification module 210 projects the surface of the two-dimensional image onto the viewing plane generating a two-dimensional rendering of the image. Inclusion identification module 210 generates a three-dimensional model of the diamond surface based on the projected set of two-dimensional renderings.

Inclusion identification module 210 identifies inclusions based on the analyzed image data (block 320), In various embodiments, inclusion identification module 210 identifies the inclusions as non-linear isolated regions on the generated surface of the diamond model. Inclusion identification module 210 communicates the identified inclusions to mapping module 220.

Mapping module 220 receives identified inclusions from inclusion identification module 210 and maps the identified inclusions to a tree structure (block 330). The mapped tree structure generated by mapping module 220 represents the identified inclusions on the surface of the diamond where the magnification is configurable for optimal encoding. Mapping module 220 communicates the mapped inclusions and magnification to encoding module 230.

Encoding module 230 encodes the received mapped inclusions (block 340) as a chain-code associated with the diamond. Encoding module 230 calculates the radial distance of the mapped inclusions (block 350) as a traced contour, in a direction, for example, counterclockwise, of the boundaries of the inclusion. The contour begins with a selected starting point, and each contour step is computed and stored. In various embodiments, encoding module 230, starts from the reference direction, and calculates the distance between the center of mass of the diamond and the center of mass of the mapped inclusions, where the contour is measured in defined angular steps and plotted as a function of the polar angle. Encoding module 230 communicates the mapped inclusions and the encoded inclusions to fingerprint generation module 240.

Fingerprint generation module 240 generates a fingerprint associated with the diamond captured by the image data based on the received image data, mapped inclusions, and encoded inclusions (block 360).

Figure 4:
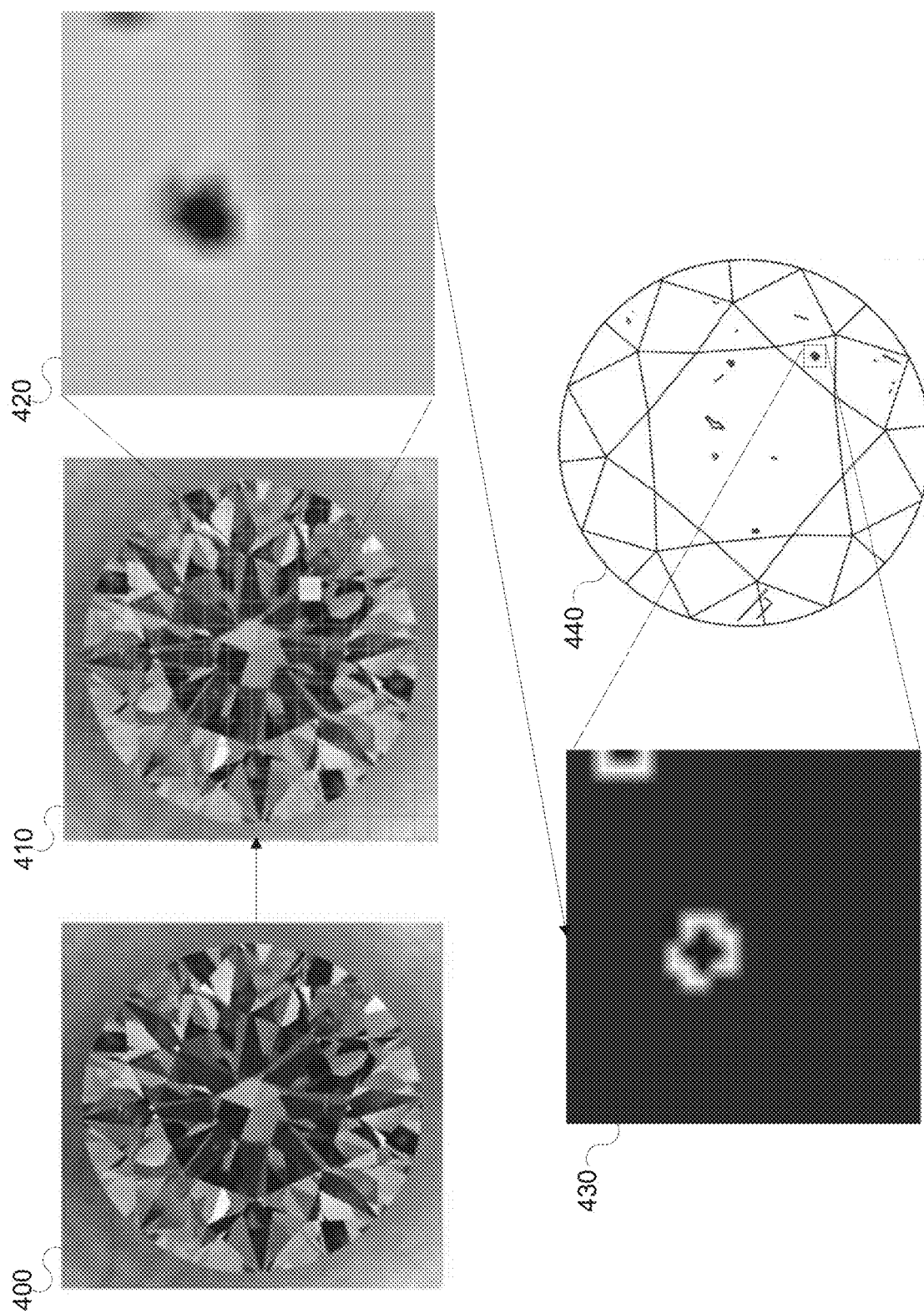
FIG. 4 depicts an illustrative block flow diagram of the analysis, mapping, and encoding of image data in accordance with an embodiment of the present invention.

The defects called inclusions in diamonds predominantly determine their grading. They look as bright or dark spots in diamond microscope images. Some examples of such defects are shown in FIG. 4, described below. A micro-lens setup, for example, imaging system 130 can be used to obtain high resolution images of diamonds and their inclusions.

FIG. 4 depicts an illustrative block flow diagram of the analysis, mapping, and encoding of image data in accordance with an embodiment of the present invention. With reference to FIGS. 1, 2, and 4, receiving module 200 may receive a set of image data associated with a diamond. An image in the set of images (block 400) may be communicated to inclusion identification module 210 for analysis.

In various embodiments, inclusion identification module 210 segments received image data (block 410) and a segment (block 420) is enlarged for inclusion identification. The image segmentation may be implemented using machine learning parameters or computer vision techniques. Image segmentation is the process of partitioning a digital image into multiple segments (sets of pixels, also known as superpixels). The goal of segmentation is to simplify and/or change the representation of an image for more efficient analysis. In various embodiments, image segmentation may be performed using convolutional neural networks where inclusion types are classified using machine learning classifiers. Image segmentation may allow the 3D position of inclusions to be determined based on 3D reconstruction from multiple segmented input images. Image segmentation is typically used to locate objects and boundaries (lines, curves, etc.) in images. More precisely, image segmentation is the process of assigning a label to every pixel in an image such that pixels with the same label share certain characteristics. The result of image segmentation is a set of segments that collectively cover the entire image, or a set of contours extracted from the image. Each of the pixels in a region are similar with respect to some characteristic or computed property, such as color, intensity, or texture. Adjacent regions are significantly different with respect to the same characteristic(s).

In various embodiments, non-linear isolated regions are identified and the identified inclusion region mapped and encoded using chain-code (block 430). In various embodiments, each segment of the segmented image is analyzed and inclusions are identified, mapped, and encoded. Fingerprint generation module 240 may generate a diamond fingerprint (block 440) based on the image data and identified, mapped, and encoded inclusions.

Figure 5:
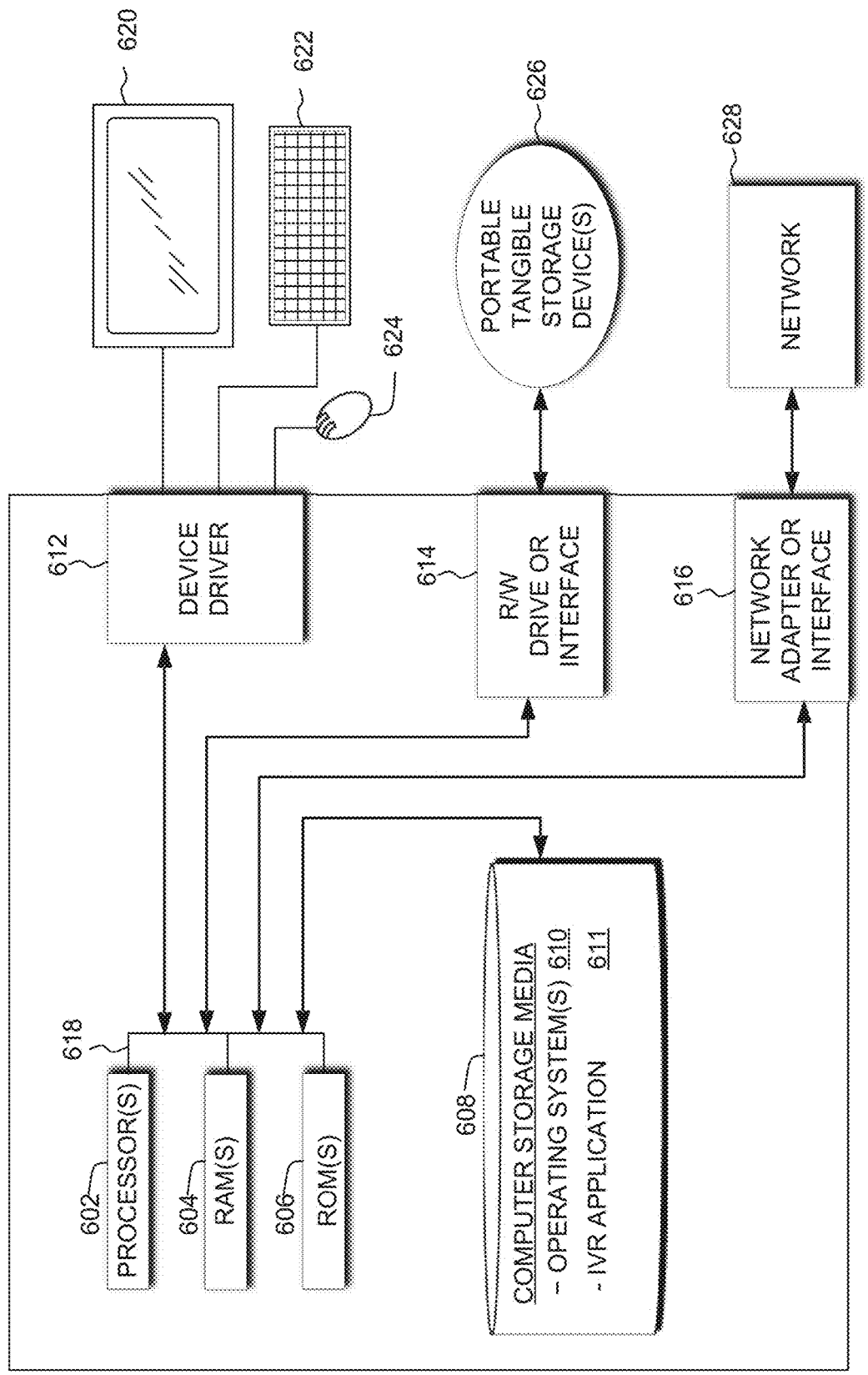
FIG. 5 depicts a block diagram of components of the server computer executing the inclusion mapping application, in accordance with an embodiment of the present invention.

FIG. 5 depicts a block diagram of components of server 110 and other components of distributed data processing environment 100 of FIG. 1, for example, user device 120, in accordance with an embodiment of the present invention. It should be appreciated that FIG. 5 provides only an illustration of one implementation and does not imply any limitations with regard to the environments in which different embodiments may be implemented. Many modifications to the depicted environment may be made.

Server 110 may include one or more processors 502, one or more computer-readable RAMs 504, one or more computer-readable ROMs 506, one or more computer readable storage media 508, device drivers 512, read/write drive or interface 514, network adapter or interface 516, all interconnected over a communications fabric 518. Communications fabric 518 may be implemented with any architecture designed for passing data and/or control information between processors (such as microprocessors, communications and network processors, etc.), system memory, peripheral devices, and any other hardware components within a system.

One or more operating systems 510, and one or more application programs 511, for example, genetic classification application 111, are stored on one or more of the computer readable storage media 508 for execution by one or more of the processors 502 via one or more of the respective RAMs 504 (which typically include cache memory). In the illustrated embodiment, each of the computer readable storage media 508 may be a magnetic disk storage device of an internal hard drive, CD-ROM, DVD, memory stick, magnetic tape, magnetic disk, optical disk, a semiconductor storage device such as RAM, ROM, EPROM, flash memory or any other computer-readable tangible storage device that can store a computer program and digital information.

Server 110 may also include an R/W drive or interface 514 to read from and write to one or more portable computer readable storage media 526. Application programs 511 on server 110 may be stored on one or more of the portable computer readable storage media 526, read via the respective R/W drive or interface 514 and loaded into the respective computer readable storage media 508.

Server 110 may also include a network adapter or interface 516, such as a TCP/IP adapter card or wireless communication adapter (such as a 4G wireless communication adapter using OFDMA technology) for connection to a network 517. Application programs 511 on Server 110 may be downloaded to the computing device from an external computer or external storage device via a network (for example, the Internet, a local area network or other wide area network or wireless network) and network adapter or interface 516. From the network adapter or interface 516, the programs may be loaded onto computer readable storage media 508. The network may comprise copper wires, optical fibers, wireless transmission, routers, firewalls, switches, gateway computers and/or edge servers.

Server 110 may also include a display screen 520, a keyboard or keypad 522, and a computer mouse or touchpad 524. Device drivers 512 interface to display screen 520 for imaging, to keyboard or keypad 522, to computer mouse or touchpad 524, and/or to display screen 520 for pressure sensing of alphanumeric character entry and user selections. The device drivers 512, R/W drive or interface 514 and network adapter or interface 516 may comprise hardware and software (stored on computer readable storage media 508 and/or ROM 506).

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature. Based on the foregoing, a computer system, method, and computer program product have been disclosed. However, numerous modifications and substitutions can be made without deviating from the scope of the present invention. Therefore, the present invention has been disclosed by way of example and not limitation.

What is claimed is:

1. A method for mapping one or more inclusions in a mineral crystal, the method comprising:
receiving a set of image data associated with the mineral crystal;
analyzing the received set of image data, wherein analyzing the received set of image data further comprises segmenting the set of image data via machine learned parameters;
identifying one or more inclusions associated with the mineral crystal based on the analyzed image data, wherein inclusions are non-linear isolated regions on a surface of the mineral crystal;

mapping the identified one or more inclusions of the mineral crystal to a tree structure representing the surface of the mineral crystal;

encoding the mapped one or more inclusions as a chain-code associated with the mineral crystal;

calculating a radial distance between a center of mass value of the mineral crystal and a center of mass value of the identified one or more inclusions; and generating a mineral crystal fingerprint, wherein the mineral crystal fingerprint is based on at least the encoded one or more inclusions and the calculated radial distance.

2. The method of claim 1, wherein the set of image data further comprises at least one of:
two-dimensional pictorial data;
three-dimensional model data; and
video data.

3. The method of claim 1, wherein encoding the mapped one or more inclusions further comprises:
plotting the radial distance as a function of a polar angle relative to the center of mass value of the identified one or more inclusions.

4. The method of claim 1, wherein the set of image data is formatted based on a predetermined resolution value and magnification value.

5. The method of claim 1, wherein the set of image data represents a measurement of visible light reflected from the surface associated with the mineral crystal, wherein a wavelength associated with the measurement of visible light is 400 nm-700 nm.

6. The method of claim 1, wherein generating a mineral crystal fingerprint further comprises:
determining a set of contours associated with the one or more inclusions, wherein each contour of the set of contours include at least a direction vector and a reference vector;
calculating a contour angle associated a difference value between the direction vector and the reference vector; and
storing the calculated contour angle in a data store.

7. The method of claim 1, wherein analyzing the received set of image data further comprises:
rotating each image of the set of image data such that a surface each image is perpendicular to a viewing plane;
projecting on the surface a set of two-dimensional renderings on the image; and
generating a three-dimensional model based on the projected set of two-dimensional renderings.

8. A computer program product for mapping one or more inclusions in a mineral crystal, the computer program product comprising:
one or more non-transitory computer-readable storage media and program instructions stored on the one or more non-transitory computer-readable storage media, the program instructions comprising:
instructions to receive a set of image data associated with the mineral crystal;
instructions to analyze the received set of image data, wherein instructions to analyze the received set of image data further comprises instructions to segment the set of image data via machine learned parameters;
instructions to identify one or more inclusions associated with the mineral crystal based on the analyzed image data, wherein inclusions are non-linear isolated regions on a surface of the mineral crystal;
instructions to map the identified one or more inclusions of the mineral crystal to a tree structure representing the surface of the mineral crystal;
instructions to encode the mapped one or more inclusions as a chain-code associated with the mineral crystal;
instructions to calculate a radial distance between a center of mass value of the mineral crystal and a center of mass value of the identified one or more inclusions; and
instructions to generate a mineral crystal fingerprint, wherein the mineral crystal fingerprint is based on at least the encoded one or more inclusions and the calculated radial distance.

9. The computer program product of claim 8, wherein the set of image data further comprises at least one of:
two-dimensional pictorial data;
three-dimensional model data; and
video data.

10. The computer program product of claim 8, wherein instructions to encode the mapped one or more inclusions further comprises:
instructions to plot the radial distance as a function of a polar angle relative to the center of mass value of the identified one or more inclusions.

11. The computer program product of claim 8, wherein the set of image data is formatted based on a predetermined resolution value and magnification value.

12. The computer program product of claim 8, wherein the set of image data represents a measurement of visible light reflected from the surface associated with the mineral crystal, wherein a wavelength associated with the measurement of visible light is 400 nm-700 nm.

13. The computer program product of claim 8, wherein instructions to generate a mineral crystal fingerprint further comprises:
instructions to determine a set of contours associated with the one or more inclusions, wherein each contour of the set of contours include at least a direction vector and a reference vector;
instructions to calculate a contour angle associated a difference value between the direction vector and the reference vector; and
instructions to store the calculated contour angle in a data store.

14. The computer program product of claim 8, wherein instructions to analyze the received set of image data further comprises:
instructions to rotate each image of the set of image data such that a surface each image is perpendicular to a viewing plane;
instructions to project on the surface a set of two-dimensional renderings on the image; and
instructions to generate a three-dimensional model based on the projected set of two-dimensional renderings.

15. A computer system for mapping one or more inclusions in a mineral crystal, the computer system comprising:
one or more computer processors;
one or more computer-readable storage media;
program instructions stored on the computer-readable storage media for execution by at least one of the one or more processors, the program instructions comprising:
instructions to receive a set of image data associated with the mineral crystal;
instructions to analyze the received set of image data, wherein instructions to analyze the received set of image data further comprises instructions to segment the set of image data via machine learned parameters;

instructions to identify one or more inclusions associated with the mineral crystal based on the analyzed image data, wherein inclusions are non-linear isolated regions on a surface of the mineral crystal;

instructions to map the identified one or more inclusions of the mineral crystal to a tree structure representing the surface of the mineral crystal;

instructions to encode the mapped one or more inclusions as a chain-code associated with the mineral crystal;

instructions to calculate a radial distance between a center of mass value of the mineral crystal and a center of mass value of the identified one or more inclusions; and instructions to generate a mineral crystal fingerprint, wherein the mineral crystal fingerprint is based on at least the encoded one or more inclusions and the calculated radial distance.

16. The computer system of claim 15, wherein the set of image data further comprises at least one of:
two-dimensional pictorial data;
three-dimensional model data; and
video data.

17. The computer system of claim 15, wherein instructions to encode the mapped one or more inclusions further comprises:
instructions to plot the radial distance as a function of a polar angle relative to the center of mass value of the identified one or more inclusions.

18. The computer system of claim 15, wherein the set of image data represents a measurement of visible light reflected from the surface associated with the mineral crystal, wherein a wavelength associated with the measurement of visible light is 400 nm-700 nm.

19. The computer system of claim 15, wherein instructions to generate a mineral crystal fingerprint further comprises:
instructions to determine a set of contours associated with the one or more inclusions, wherein each contour of the set of contours include at least a direction vector and a reference vector;
instructions to calculate a contour angle associated a difference value between the direction vector and the reference vector; and
instructions to store the calculated contour angle in a data store.

20. The computer system of claim 15, wherein instructions to analyze the received set of image data further comprises:
instructions to rotate each image of the set of image data such that a surface each image is perpendicular to a viewing plane;
instructions to project on the surface a set of two-dimensional renderings on the image; and
instructions to generate a three-dimensional model based on the projected set of two-dimensional renderings.

* * * * *